US008322192B2

(12) United States Patent
Jones et al.

(10) Patent No.: US 8,322,192 B2
(45) Date of Patent: Dec. 4, 2012

(54) SENSOR APPARATUS AND METHOD THEREFOR

(75) Inventors: Beth A. Jones, Hook (GB); Paul Rennie, Bracknell (GB); Robert Pallant, Slough (GB); Paul D. Smith, Brighton (GB)

(73) Assignee: Kidde Technologies, Inc., Wilson, NC (US)

( * ) Notice: Subject to any disclaimer, the term of this patent is extended or adjusted under 35 U.S.C. 154(b) by 275 days.

(21) Appl. No.: 12/692,205

(22) Filed: Jan. 22, 2010

(65) Prior Publication Data

US 2011/0138881 A1 Jun. 16, 2011

(30) Foreign Application Priority Data

Dec. 14, 2009 (GB) .................................. 0921842.1

(51) Int. Cl.
*G01N 7/10* (2006.01)
(52) U.S. Cl. ......................... 73/31.06; 438/15
(58) Field of Classification Search ................. 73/31.06; 438/15
See application file for complete search history.

(56) References Cited

U.S. PATENT DOCUMENTS

| | | | |
|---|---|---|---|
| 3,754,375 A | 8/1973 | Bouchilloux et al. | |
| 3,864,628 A * | 2/1975 | Klass et al. | 324/71.1 |
| 4,253,302 A * | 3/1981 | Asano et al. | 60/276 |
| 4,608,549 A | 8/1986 | Fukui | |
| 4,631,075 A * | 12/1986 | Yamabe et al. | 96/13 |
| 4,677,414 A * | 6/1987 | Yates | |
| 4,877,528 A * | 10/1989 | Friesen et al. | 210/500.29 |
| 5,279,795 A | 1/1994 | Hughes et al. | |
| 5,849,165 A | 12/1998 | Kojima et al. | |
| 6,012,327 A | 1/2000 | Seth et al. | |
| 6,499,335 B2 | 12/2002 | Nomura et al. | |
| 6,513,364 B1 | 2/2003 | Jonda et al. | |
| 7,140,229 B2 * | 11/2006 | Stromereder et al. | 73/23.2 |
| 7,156,967 B2 | 1/2007 | Hotta et al. | |
| 7,228,725 B2 | 6/2007 | Salter et al. | |
| 7,266,991 B2 | 9/2007 | Bley | |
| 7,321,287 B2 | 1/2008 | Ota et al. | |
| 7,479,255 B2 | 1/2009 | Otani et al. | |
| 7,491,547 B1 | 2/2009 | Warburton | |
| 2006/0120920 A1 | 6/2006 | Rue | |
| 2006/0194332 A1 | 8/2006 | Wado et al. | |
| 2006/0237316 A1 | 10/2006 | Clyde et al. | |
| 2007/0089989 A1 | 4/2007 | Hoagland | |
| 2008/0274559 A1 | 11/2008 | Fleischer et al. | |

(Continued)

FOREIGN PATENT DOCUMENTS

EP        1720008        11/2006

(Continued)

OTHER PUBLICATIONS

Extended European Search Report dated Apr. 4, 2011.

(Continued)

*Primary Examiner* — Hezron E Williams
*Assistant Examiner* — Paul West
(74) *Attorney, Agent, or Firm* — Carlson, Gaskey & Olds PC

(57) ABSTRACT

A sensor apparatus includes a metal oxide semiconductor sensor and a housing having an internal chamber in which the sensor is disposed. The housing includes at least one window for the ingress of a gas into the internal chamber from an atmosphere exterior to the housing. A gas-selective barrier is disposed across the at least one window.

25 Claims, 1 Drawing Sheet

FOREIGN PATENT DOCUMENTS

| | | |
|---|---|---|
| EP | 2098281 | 9/2009 |
| JP | 2000338072 | 5/1999 |
| JP | 2008014662 | 7/2006 |
| WO | 2008076602 | 6/2008 |

OTHER PUBLICATIONS

UK Search Report and Examination Report for GB0921842.1 (7 pages).

Examiner's Report No. 2 dated Jun. 7, 2012.

Van 'T Hoff J.A. et al., "Preparation of asymmetric gas separation membranes with high selectivity by a dual-bath coagulation method", Journal of Membrane Science, 70, pp. 17-30, 1992, Elsevier Science Publishers B.V., Amsterdam.

* cited by examiner

SENSOR APPARATUS AND METHOD THEREFOR

RELATED APPLICATION

This application claims priority to GB Patent Application No. 0921842.1, which was filed Dec. 14, 2009.

BACKGROUND

This disclosure relates to a sensor apparatus for measuring a gas concentration in a surrounding environment.

Metal oxide semiconductor ("MOS") sensors and other types of sensors are known and used for detecting gas concentration levels. For instance, MOS sensors are sensitive to a variety of different gases, such as methane, hydrogen, ethanol, isobutane, etc.

SUMMARY

A disclosed sensor apparatus includes a metal oxide semiconductor sensor and a housing having an internal chamber in which the sensor is disposed. The housing includes at least one window for the ingress of a gas into the internal chamber from an atmosphere exterior to the housing. A gas-selective barrier is disposed across the at least one window.

An example method for use with the sensor apparatus includes impeding the ingress of a selected species of flammable gas through the at least one window using the gas-selective barrier in the window.

In another aspect, a sensor apparatus includes a sensor, a sensor zone around the sensor for receiving analyte gas, and a gas-selective barrier between the sensor zone and an atmosphere exterior to the sensor zone.

BRIEF DESCRIPTION OF THE DRAWINGS

The various features and advantages of the disclosed examples will become apparent to those skilled in the art from the following detailed description. The drawings that accompany the detailed description can be briefly described as follows.

DETAILED DESCRIPTION OF THE PREFERRED EMBODIMENT

Figure 1:
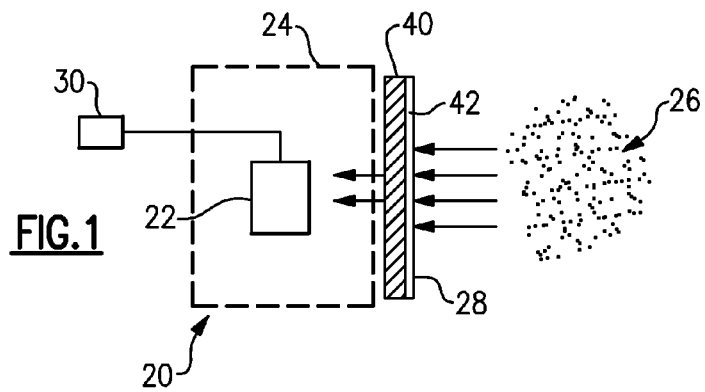
FIG. 1 illustrates an example sensor apparatus.

FIG. 1 illustrates selected portions of an example sensor apparatus 20 that is adapted to have increased selectivity to a preferred species of flammable gas, such as hydrogen. For instance, the sensor apparatus 20 may be used in an environment that may contain many different species of flammable gases. In the case of a vehicle (e.g., a commercial bus or other transportation device) that utilizes hydrogen for propulsion, enhanced hydrogen detection may be desired. Most metal oxide semiconductor ("MOS") sensors are typically more sensitive to other flammable gases in the surrounding environment than to hydrogen, which can interfere with obtaining reliable hydrogen concentration measurements. However, as will be described, the sensor apparatus 20 is configured to have heightened selectivity to hydrogen and may thereby be used to more reliably detect any hydrogen that escapes from hydrogen storage in a vehicle, for example.

In the illustrated example, the sensor apparatus 20 includes a metal oxide semiconductor ("MOS") sensor 22 (e.g. Figaro TGS2611) and a sensor zone 24 around the MOS sensor 22 for receiving analyte gas 26 from an atmosphere that is exterior to the sensor zone 24. The MOS sensor 22 may include a gas-sensing surface (not shown) composed of tin oxide ($SnO_2$), for example. The sensor apparatus 20 further includes a gas-selective barrier 28 disposed between the sensor zone 24 and the exterior atmosphere for impeding ingress of a selected species of flammable gas into the sensor zone 24. For instance, "gas-selective" may refer to a characteristic of preferentially hindering movement of one species of flammable gas over another. In the case of a vehicle application where detection of hydrogen is desired, the gas-selective barrier 28 is adapted to impede ingress of other types of gases, such as methane, to thereby increase relative selectivity of the MOS sensor 22 to hydrogen.

The MOS sensor 22 may be electrically connected to a controller 30 for transmitting signals that are representative of detected gas concentrations in the sensor zone 24 to the controller 30. The controller 30 may include hardware, software, or both for receiving and processing the signals. As an example, the controller 30 may trigger an alarm or other indication in response to the received signals if the detected gas concentration exceeds a predetermined threshold.

The gas-selective barrier 28 may include a support 40 and an organosilicon coating 42 disposed on the support 40. In this case, there is a single layer of the organosilicon coating 42 on the support 40. However, in other examples, the support 40 may include multiple layers of the organosilicon coating 42 on one side or layers of the organosilicon coating 42 on the opposed sides of the support 40 to achieve a desired gas-selectivity.

The support 40 is porous but mechanically suitable for supporting the organosilicon coating 42. In some examples, the support 40 may be cellulose paper or a polymer material, such as a membrane, woven fiber structure or non-woven fiber structure of polytetrafluoroethylene fibers. The support 40 may have a degree of porosity that is suited for the particular application. For instance, a higher degree of porosity may be selected to facilitate avoiding substantially impeding movement of the analyte gas 26 such that the organosilicon coating 42 is the sole component of the gas-selective barrier 28 that functions to impede gas ingress. Alternatively, a lower degree of porosity may be selected to compliment the gas-selectivity of the organosilicon coating 42 by trapping or impeding larger gas molecules, such as methane. In this regard, the cellulose paper may have a weight of 50-75 $g/m^2$.

In the above examples, the amount of the organosilicon coating 42 may be controlled to achieve a desired influence on impedance. For instance, using a greater amount may provide a greater degree of impedance while using less may provide less impedance. In some examples, the amount may be 0.1-10 $g/m^2$. In a further example that may be useful in hydrogen vehicle applications, the amount may be 0.5-2.0 $g/m^2$. The amount may also be represented by a thickness of the organosilicon coating 42. In some examples, the thickness may be 0.5-10 micrometers. In a further example, the thickness may be approximately 0.5-2.0 micrometers.

The organosilicon coating 42 may be of a type that impedes methane gas movement more than it impedes hydrogen gas movement. For instance, the organosilicon coating 42 may be polydimethylsiloxane, polydiethylsiloxane, polyalkylene oxide siloxane, phenylmethylsiloxane-dimethylsiloxane copolymer, diphenylsiloxane-dimethylsiloxane copolymer and combinations thereof. Given this description, one of ordinary skill in the art will recognize other types of organosilicon or silicone materials to meet their particular needs.

MOS sensors may be more sensitive to methane than to hydrogen at relatively low concentrations of hydrogen and methane below approximately 5 vol %. In this concentration regime, exposure to low levels of methane may cause a significant electrical response signal from a MOS sensor. In this regard, the gas-selective barrier 28 impedes the ingress of methane into the sensor zone 24 to thereby increase the selectivity of the MOS sensor 22 to hydrogen and facilitate reducing interference from methane and other gases. The gas-selective barrier 28 may also be used to impede the ingress of methane to reduce exposure of the MOS sensor 22 to transient increases in concentration of methane that might otherwise cause a significant electrical response signal that could trigger an alarm or other indicator.

Figure 2:
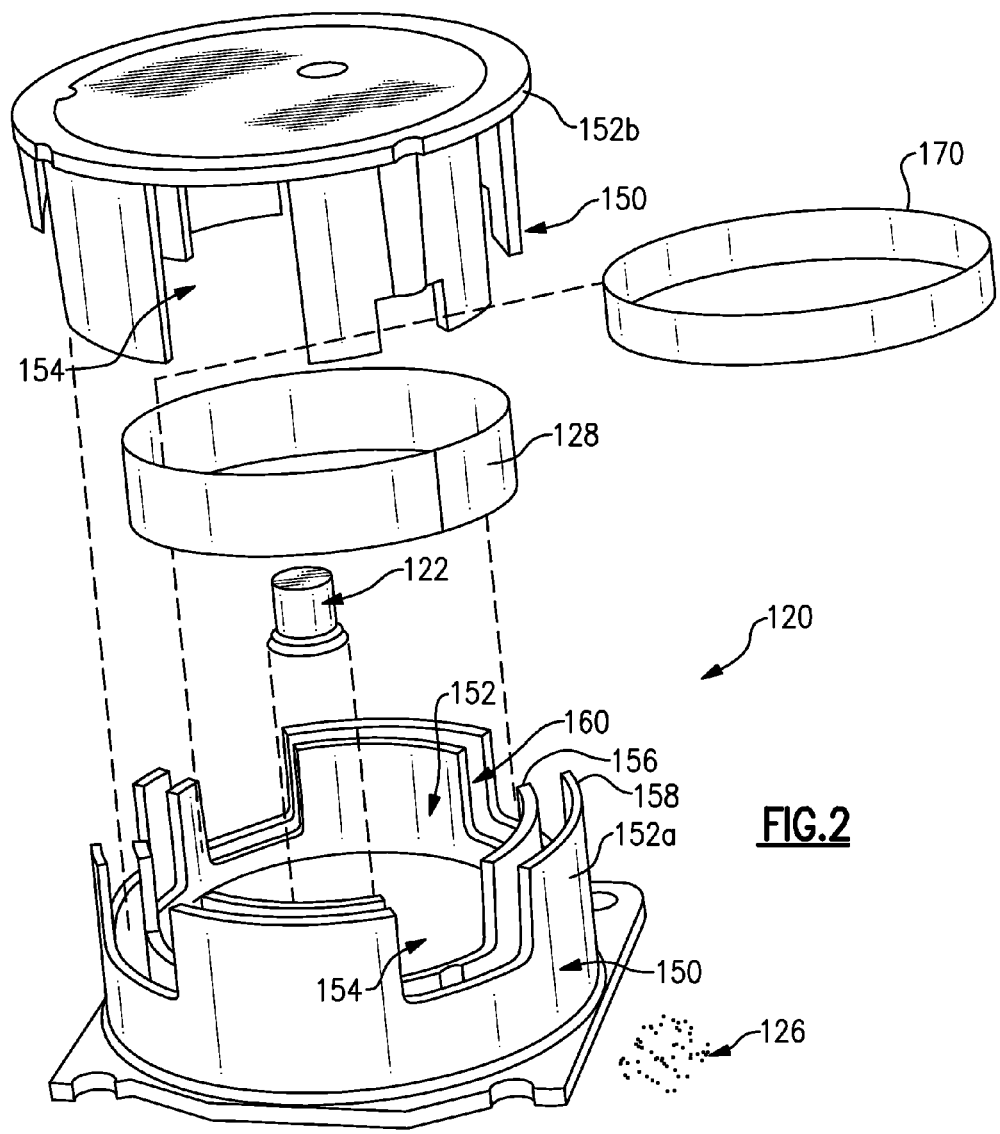
FIG. 2 illustrates another example sensor apparatus.

FIG. 2 illustrates another example sensor apparatus 120 that is also adapted for increased selectivity to a preferred species of flammable gas, such as hydrogen. In this disclosure, like reference numerals designate like elements where appropriate, and reference numerals with the addition of one-hundred or multiples thereof designate modified elements that are understood to incorporate the same features and benefits of the corresponding original elements.

In this example, the sensor apparatus 120 includes a MOS sensor 122 and a housing 150 having an internal chamber 152 in which the MOS sensor 122 is disposed. The internal chamber 152 may be considered to be similar to the sensor zone 24 of the prior examples, for receiving analyte gas 126. The housing 150 includes at least one window 154 for the ingress of analyte gas 126 into the internal chamber 152 from an atmosphere that is external to the housing 150.

A gas-selective barrier 128 is disposed within the at least one window 154. In this case, the housing 150 includes four such windows 154. However, in other examples, there may be fewer or more windows 154 depending upon the detection needs of the particular application. As in the previous example, the MOS sensor 122 may be electrically connected to a controller (not shown) for transmitting signals representative of detected gas concentrations.

The housing 150 may include a base 152*a* and a cover 152*b* that fits with the base 152*a* to form the housing 150. The base 152*a* includes an inner wall 156 and an outer wall 158 that are spaced apart to define circumferential slot 160 therebetween. In the illustrated example, the base 152*a* is circular and thus the slot 160 is circumferential. However, in other examples the base 152*a* may have a different shape and the slot 160 may have a shape that corresponds to the shape of the base 152*a*.

The inner and outer walls 156 and 158 at least partially frame the window or windows 154. In this case, the walls 156 and 158 of the base 152*a* form three sides of each window 154 and the cover 152*b* forms a fourth side. The windows 154 may be cut into the walls 156 and 158 or formed in a molding process or the like.

The gas-selective barrier 128 is in the shape of a ring and may be disposed within the internal chamber 152 such that the gas-selective barrier 128 extends across the windows 154. The cover 152*b* may then be received within the slot 160 of the base 152*a* such that the windows 154 in the cover 152*b* align with the windows 154 in the base 152*a*. In some examples, additional filters 170 may be disposed adjacent to the gas-selective barrier 128 to provide other services, such as limiting debris or liquid from entering into the internal chamber 152. Such filters 170 may also be a ring that fits concentrically with the gas-selective barrier 128.

In one example of the effectiveness of the gas-selective barrier 128, the sensor apparatus 120 was exposed to an analyte gas having a 50% LEL (lower explosion limit) concentration of flammable gas, approximately 2.5 vol % methane or 2.0 vol % hydrogen. The time for the MOS sensor 122 to reach 90% of the full scale sensitivity output, which is also known as $t_{90}$, was measured and compared to the same arrangement without the gas-selective barrier 128. In this case, the gas-selective barrier 128 caused a larger delay in the response time to methane gas than to the hydrogen gas. Thus, the gas selective barrier 128 selectively impedes the ingress of methane into the internal chamber 152 such that the relative selectivity of the sensor apparatus 120 to hydrogen is increased.

Although a combination of features is shown in the illustrated examples, not all of them need to be combined to realize the benefits of various embodiments of this disclosure. In other words, a system designed according to an embodiment of this disclosure will not necessarily include all of the features shown in any one of the Figures or all of the portions schematically shown in the Figures. Moreover, selected features of one example embodiment may be combined with selected features of other example embodiments.

The preceding description is exemplary rather than limiting in nature. Variations and modifications to the disclosed examples may become apparent to those skilled in the art that do not necessarily depart from the essence of this disclosure. The scope of legal protection given to this disclosure can only be determined by studying the following claims.

What is claimed is:

1. A sensor apparatus comprising:
   a metal oxide semiconductor ("MOS") sensor;
   a housing having an internal chamber in which the MOS sensor is disposed, the housing having at least one window for the ingress of gas into the internal chamber from an atmosphere exterior to the housing; and
   a gas-selective barrier disposed across the at least one window, wherein the gas-selective barrier is a support having an organosilicon coating thereon, the support being cellulose paper, the cellulose paper having a weight of 50-75 $g/m^2$ and the organosilicon coating being present in an amount of 0.1-200 $g/m^2$ such that the gas-selective barrier impedes methane at concentrations of hydrogen and methane below approximately 5 volume percent and increases hydrogen selectivity of the MOS sensor relative to the methane.

2. The sensor apparatus as recited in claim 1, wherein the gas-selective barrier is a ring disposed within the housing.

3. The sensor apparatus as recited in claim 1, wherein the organosilicon coating is polydiethylsiloxane.

4. The sensor apparatus as recited in claim 1, including an amount of 0.1-10 $g/m^2$ of the organosilicon coating.

5. The sensor apparatus as recited in claim 1, wherein the organosilicon coating has a thickness of 0.5-10 micrometers.

6. The sensor apparatus as recited in claim 1, wherein the organosilicon coating is phenylmethylsiloxane-dimethylsiloxane copolymer.

7. The sensor apparatus as recited in claim 1, wherein the organosilicon coating is diphenylsiloxane-dimethylsiloxane.

8. A sensor apparatus comprising:
   a metal oxide semiconductor ("MOS") sensor;
   a housing having an internal chamber in which the MOS sensor is disposed, the housing having a base with a plurality of windows arranged around the MOS sensor for the ingress of gas into the internal chamber from an atmosphere exterior to the housing, the base having an inner wall and an outer wall forming a slot therebetween and each of the plurality of windows is at least partially framed by the inner wall and the outer wall; and
   a gas-selective barrier disposed across the at least one window.

9. The sensor apparatus as recited in claim 8, wherein the gas-selective barrier is a support having an organosilicon coating.

10. The sensor apparatus as recited in claim 9, wherein the support is cellulose paper.

11. The sensor apparatus as recited in claim 10, wherein the cellulose paper has a weight of 50-75 g/m$^2$.

12. The sensor apparatus as recited in claim 9, wherein the support is a polymeric material.

13. The sensor apparatus as recited in claim 8, further including other filters adjacent to the gas-selective barrier.

14. The sensor apparatus as recited in claim 8, wherein the gas-selective barrier is a support having an organosilicon coating thereon, the support being cellulose paper, the cellulose paper having a weight of 50-75 g/m$^2$ and the organosilicon coating being present in an amount of 0.1-200 g/m$^2$ such that the gas-selective barrier impedes methane at concentrations of hydrogen and methane below approximately 5 volume percent and increases hydrogen selectivity of the MOS sensor relative to the methane.

15. The sensor apparatus as recited in claim 8, wherein the gas-selective barrier is a ring.

16. The sensor apparatus as recited in claim 8, wherein the slot is circumferential.

17. The sensor apparatus as recited in claim 8, further including a cover received within the slot, the cover having a plurality of windows that align with, respectively, the plurality of windows of the base.

18. The sensor apparatus as recited in claim 8, further including a cover, and the cover and the gas-selective barrier are within the slot.

19. The sensor apparatus as recited in claim 8, further including a filter that is arranged concentrically with the gas-selective barrier.

20. A method for use with a sensor apparatus that includes a metal oxide semiconductor ("MOS") sensor and a housing having an internal chamber in which the MOS sensor is disposed, the housing having at least one window for the ingress of gas into the internal chamber, the method comprising:

impeding the ingress of methane through the at least one window using a gas-selective barrier disposed within the at least one window, wherein the gas-selective barrier is a support having an organosilicon coating thereon, the support being cellulose paper, the cellulose paper having a weight of 50-75 g/m$^2$ and the organosilicon coating being present in an amount of 0.1-200 g/m$^2$ such that the gas-selective barrier impedes the methane at concentrations of hydrogen and methane below approximately 5 volume percent and increases hydrogen selectivity of the MOS sensor relative to the methane.

21. The method as recited in claim 20, including impeding the ingress of methane as the selected species of flammable gas to reduce exposure of the MOS sensor to transient increases in concentration of methane in an atmosphere exterior to the housing.

22. A sensor apparatus comprising:
a metal oxide semiconductor ("MOS") sensor;
a sensor zone around the MOS sensor for receiving analyte gas; and
a gas-selective barrier between the sensor zone and an atmosphere exterior to the sensor zone, wherein the gas-selective barrier is a support having an organosilicon coating thereon, the support being cellulose paper, the cellulose paper having a weight of 50-75 g/m$^2$ and the organosilicon coating being present in an amount of 0.1-200 g/m$^2$ such that the gas-selective barrier impedes methane at concentrations of hydrogen and methane below approximately 5 volume percent and increases hydrogen selectivity of the MOS sensor relative to the methane.

23. The sensor apparatus as recited in claim 22, including an amount of 0.1-10 g/m$^2$ of the organosilicon coating.

24. The sensor apparatus as recited in claim 22, wherein the organosilicon coating has a thickness of 0.5-10 micrometers.

25. The sensor apparatus as recited in claim 22, wherein the organosilicon coating is selected from a group consisting of polydimethylsiloxane, polydiethylsiloxane, polyalkylene oxide siloxane, phenylmethylsiloxane-dimethylsiloxane copolymer, diphenylsiloxane-dimethylsiloxane copolymer, and combinations thereof.

\* \* \* \* \*